United States Patent [19]

Blasband

[11] Patent Number: 5,384,025
[45] Date of Patent: Jan. 24, 1995

[54] NOTCHED SPACER FOR SLAB-GEL ELECTROPHORESIS

[75] Inventor: Andrew J. Blasband, Redwood City, Calif.

[73] Assignee: Applied Biosystems, Inc., Foster City, Calif.

[21] Appl. No.: 206,995

[22] Filed: Mar. 7, 1994

[51] Int. Cl.6 .............................................. C25B 9/00
[52] U.S. Cl. ............................................... 204/299 R
[58] Field of Search ................................... 204/299 R

[56] References Cited

U.S. PATENT DOCUMENTS 4,762,743 8/1988 von Alven et al. ............. 204/299 R
4,811,218 6/1986 Hunkapiller et al. .

OTHER PUBLICATIONS

Trainor Anal. Chem., 62: 418–426, 1990 DNA Sequencing, Automation, and the Human Genome.
Watkins Biotechniques, 6: 310–319, 1988 Restriction Fragment Length Polymorphism (RFLP): Applications in Human Chromosome Mapping and Genetic Disease Research.

Primary Examiner—John Niebling
Assistant Examiner—C. Delacroix-Muirheid
Attorney, Agent, or Firm—Paul D. Grossman

[57] ABSTRACT

The present invention is directed to improved side spacers for use in slab gel electrophoresis that prevent the formation of channels between the electrophoresis gel and the side spacer and methods employing the side spacer. The improvement consists of forming the side spacer with one or more notches cut into the edge of the side spacer in contact with the gel, such that, when the gel hardens, the side spacer is anchored into the gel, thereby preventing the formation of channels between the side spacer and the gel.

12 Claims, 4 Drawing Sheets

NOTCHED SPACER FOR SLAB-GEL ELECTROPHORESIS

FIELD OF THE INVENTION

The present invention relates to electrophoresis systems, and in particular to an improved side spacer for use with slab gel electrophoresis, and methods employing the side spacer.

BACKGROUND OF THE INVENTION

Electrophoresis has been and continues to be a dominant analytical separation technique in the biological sciences. This is because electrophoresis is particularly well suited for biopolymers, e.g. DNA, proteins, carbohydrates, and the like, which are typically of high molecular weight, water soluble, labile and charged. Modern applications of gel electrophoresis range from the molecular weight determination of proteins, e.g. Hames et al. eds., Gel Electrophoresis of Proteins, IRL Press, Washington, D.C.(1984), to DNA sequencing, e.g. Trainor, Anal. Chem., 62: 418–426 (1990), to the diagnosis of genetic disease, e.g. Watkins, Biotechniques, 6: 310 –319 (1988), to the analysis of carbohydrate mixtures, e.g. Jackson, et al., Electrophoresis, 12: 94 –96 (1991).

Typically, analytical electrophoresis is performed in a "slab" format. The technique of slab gel electrophoresis is well known in the art of biochemistry and molecular biology, e.g. Rickwood et al., eds., Gel Electrophoresis of Nucleic Acids: A Practical Approach, IRL Press, New York, (1990). In slab gel electrophoresis, an electrophoretic separation medium, typically a cross-linked gel, is placed between two rectangular non-conducting plates, e.g. glass plates, which are separated by two side spacers located at the side edge regions of the plates, thereby forming a "gel sandwich". The side spacers ensure that the distance between the glass plates is uniform across the gel, thereby ensuring a uniform gel thickness. The top and bottom edges of the gel sandwich are immersed in buffer solutions which are contained in top and bottom buffer reservoirs. Top and bottom electrodes are mounted within top and bottom buffer reservoirs. The purpose of the buffer solutions is to provide electrical contact between the top and bottom electrodes and the top and bottom edges of the gel sandwich. Sample is loaded onto the top of the gel, and an electrical potential is applied across the gel, causing the charged sample to move through the gel. Automated slab-gel electrophoresis systems additionally include a real-time-scanning fluorescence detector, e.g. Hunkapiller et al., U.S. Pat. No. 4,811,218 to detect multiple fluorescently labeled samples as they travel through the gel. In order to collect data from multiple lanes during electrophoresis, the optical detector system is scanned across the width of the gel in a direction perpendicular to the direction of migration of the fluorescently labeled samples.

It is important to the proper functioning of the slab gel electrophoresis process that the side spacers remain in contact with the electrophoresis gel throughout the analysis, i.e. that no voids or channels appear between the side spacers and the gel. Such voids can lead to a variety of problems including electrical short circuits, non-homogenous electric fields, destruction of the gel, and, in some extreme cases, fire. The present invention is directed towards apparatus and methods which ensure intimate contact between the side spacer and the electrophoresis gel, thereby reducing the likelihood of void formation and the resulting complications.

SUMMARY OF THE INVENTION

Briefly, the present invention is directed to an improved side spacer for use in slab gel electrophoresis that prevents the formation of channels between the electrophoresis gel and the side spacer, and methods employing the improved side spacer. The improvement consists of forming the side spacer with notches cut into the edge of the side spacer in contact with the gel, such that, when the gel hardens, the side spacer is anchored into the gel, thereby preventing the formation of channels between the side spacer and the gel.

More particularly, the side spacer of the present invention comprises an inside edge which contacts a gel layer, the inside edge having at least one notch therein which inscribes a region of the gel layer, thereby anchoring the side spacer into the gel layer and preventing the formation of micro-channels between the gel layer and the side spacer.

Additionally, the present invention includes an electrophoresis gel sandwich, comprising a pair of juxtaposed flat plates with a gel layer therebetween, and a pair of side spacers for spacing the plates apart and parallel to each other, having at least one notch wherein the notch inscribes a region of the gel layer, thereby anchoring the side spacer into the gel layer.

Finally, the present invention includes a method of assembling an electrophoresis gel sandwich comprising the steps of (i) laying down a first plate of a pair, (ii) placing a pair of notched side spacers on top of the first plate such that an outside edge of the notched side spacers are flush with the edges of the first plate, and the notches of each notched side spacer are facing one another; (iii) placing a second plate of said pair on top of the notched side spacers with the edges of the second plate flush with the edges of the first plate and the outside edge of the spacers, thereby forming a slot between the two plates, (iv) attaching a clamping means to maintain the above mentioned configuration, and (v) pouring a gel medium into the slot formed between the two plates, wherein when the gel medium become rigid, a gel layer is formed between the two plates.

DETAILED DESCRIPTION OF THE INVENTION

Figure 1:
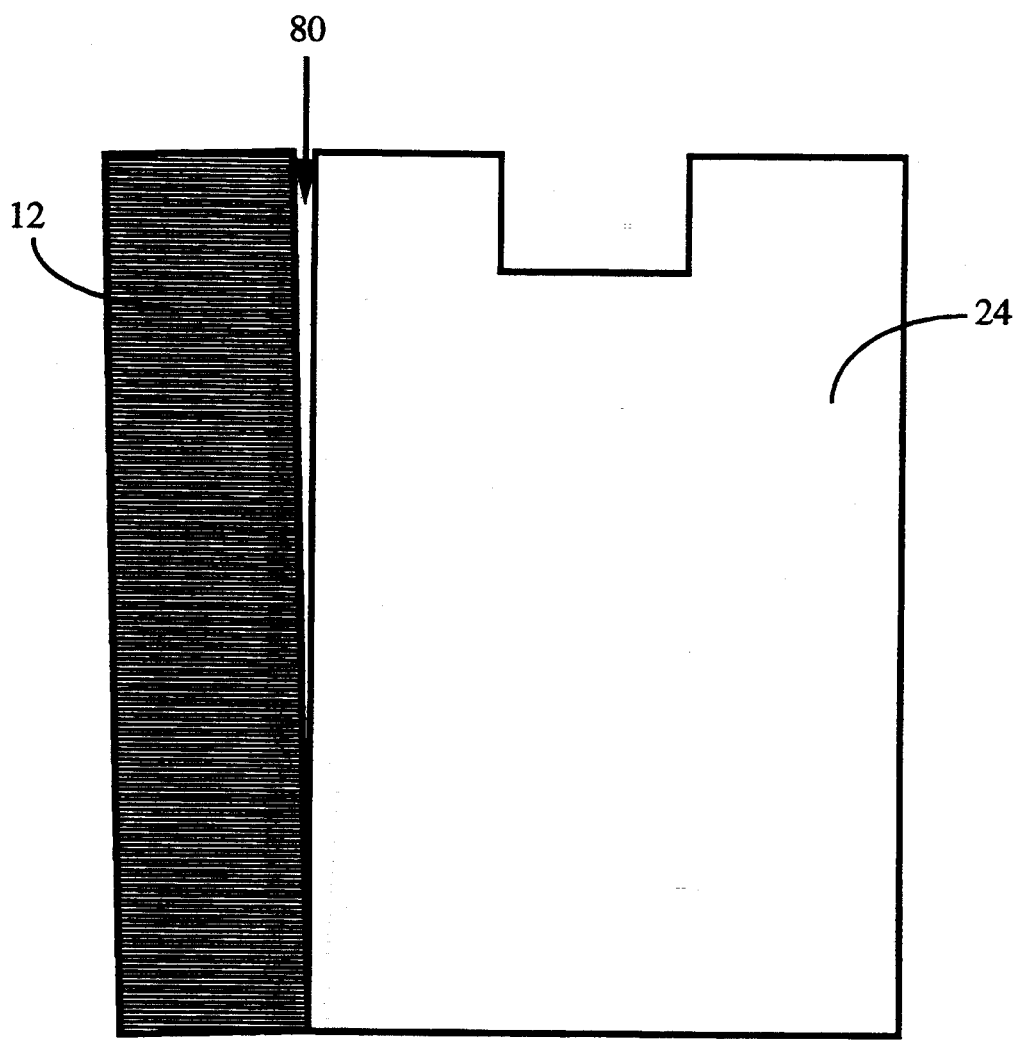
FIG. 1 show a micro-channel between a side spacer and a gel layer.

An important aspect of the present invention is the discovery that side spacer (12) can be accidentally dislodged prior to electrophoresis due to handling of the gel sandwich, leading to the formation of a micro-channel (80) between gel layer (24) and side spacer (12). See FIG. 1. Micro-channels have been found to be the cause of several serious problems which can limit the utility of slab gel electrophoresis. First, micro-channels can cause leaking of buffer solution from the top buffer reservoir, leading to a reduced liquid level in the top reservoir. As the liquid level in the top reservoir drops, the voltage-drop between top electrode and the gel layer can increase, thereby reducing the voltage drop across the gel, possibly leading to variable electrophoretic velocities of the sample molecules. In the extreme case, where the liquid level in the top reservoir falls below the top edge of the gel layer, the electrical connection between the gel layer and the top electrode can be severed, causing a short circuit between the top electrode and the gel layer. A short circuit can result in arcing between the top electrode and the exposed gel layer, which in some cases can lead to fire.

Second, micro-channels (80) can create a path of low electrical resistance between gel layer (24) and side spacers (12). This low-resistance path can disrupt the electric field lines within gel layer (24), thereby affecting the migration direction and velocity of the sample molecules, leading to non-parallel and non-horizontally aligned electrophoresis lanes. These deformed lanes can complicate the task of data interpretation, particularly in the case of automated real-time data collection systems, e.g. fluorescence-based DNA sequencing systems.

Third, because of high currents within the low resistance micro-channels, a "hot-zone" can be created within the micro-channels due to Joule heating. The elevated temperature within these hot-zones can lead to degassing of the electrophoresis buffer, ultimately leading to bubble formation. Arching can occur across the bubbles, leading to destruction of the gel layer and, in extreme cases, fire.

Another important aspect of the present invention is an improved design for a side spacer which resists dislodgment by anchoring itself into the gel layer, thereby reducing the likelihood of problems associated with micro-channeling between the side spacer and the gel layer. This anchoring is achieved by forming a "lock notch" in the spacer, where a lock notch is defined herein as a cut, indentation or hollow formed into the edge of the side spacer facing the gel layer. Hereinafter, a side spacer incorporating a lock notch will be referred to as a lock notch-spacer. Lock-notch spacers can incorporate a plurality of lock notches. A convenient way to characterize a lock notch of the present invention is by reference to a "hold area", wherein the hold area is defined as the area of the gel layer which is inscribed by the lock notch. The preferred hold area will depend on the nature of the gel material, e.g. percent polymer and crosslinker. Preferably, the lock notch of the present invention should have a hold area of between about $1*10^{-6}$ m$^2$ and $1.2*10^{-3}$ m$^2$. More preferably, at least one lock notch of the present invention should be located within 20 cm of the top and bottom edge of the side spacer.

Figures 2A, 2B:
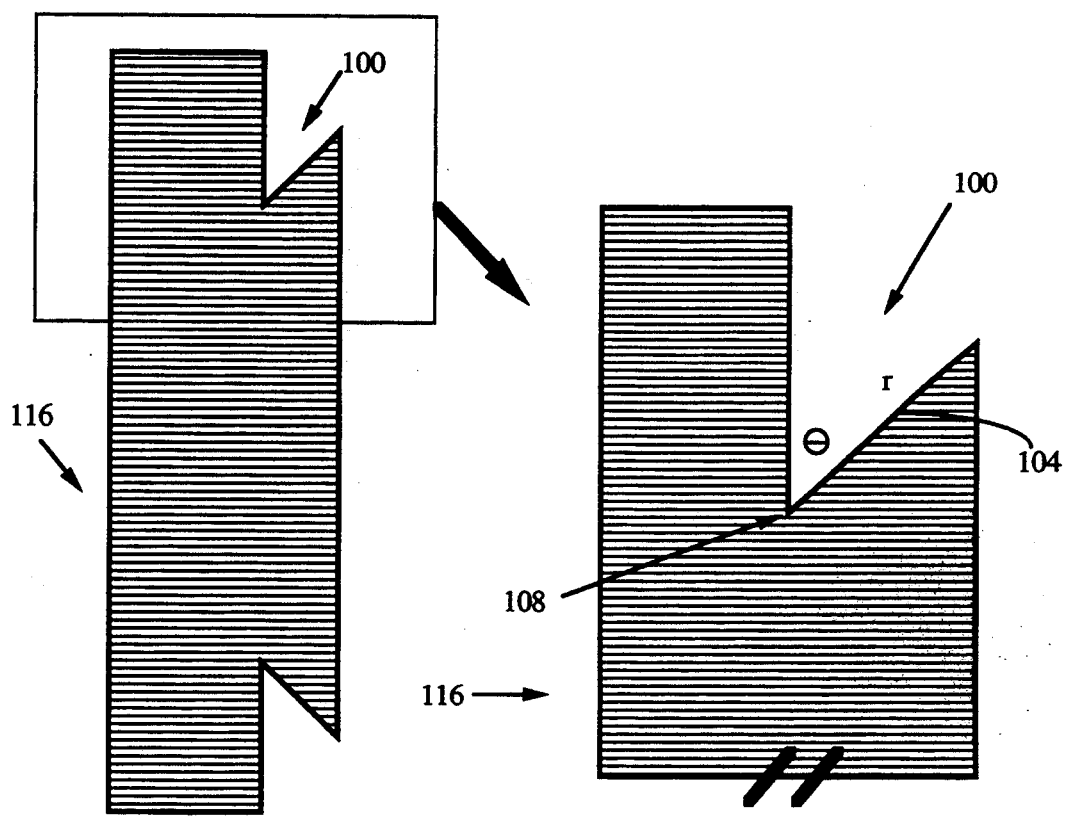
FIG. 2 show a preferred embodiment of the side spacer of the present invention.
Figure 3D:
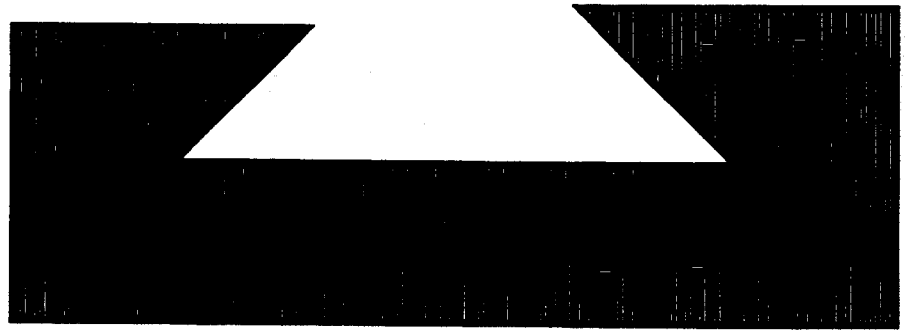
FIG. 3 shows several alternative embodiments of the side spacer of the present invention.
Figure 3C:
Figure 3B:
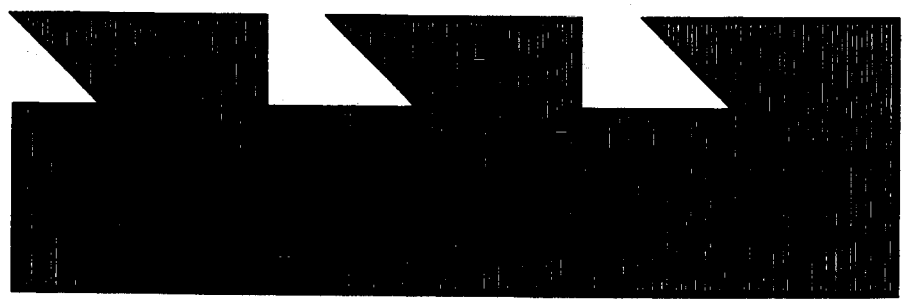
Figure 3A:
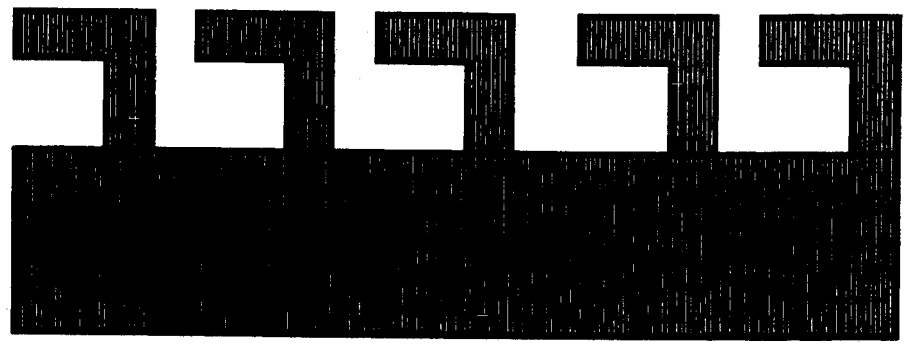

One preferred configuration of the lock notch of the present invention is a "triangular" lock notch, see FIG. 2, wherein triangular-lock notch (100) can be described by reference to notch edge (104) having length r, and notch angle (108), having a magnitude of $\theta$. In the case of triangular-lock notch (100), notch edge (104) should have a length of between 5 mm and 50 mm. Preferably, notch edge (104) should have a length of between 10 mm and 30 mm Notch angle (108) should be an acute angle. Preferably, notch angle (108) is between 5° and 85°. More preferably notch angle (108) is between 10° and 75°. As will be shown below, most preferably notch angle (108) is 45°. In the case of a triangular-lock notch, the hold area is equal to $(r^2/2) * \sin(\theta) \cos(\theta)$. A notch angle of 45° will maximize the hold area of a triangular-lock notch, one with ordinary skill in the art will recognize that the concept of a hold area is applicable to geometries other than the triangular geometry. FIG. 3 shows several possible alternative lock notch configurations.

The material for the side spacer of the present invention should be capable of being formed into thin sheets having a defined uniform thickness to ensure a uniform gel layer, non-electrically conducting, non-compressible, and chemically inert with respect to common gel materials and aqueous buffer solutions. Examples of such materials include polycarbonate, polyvinylchloride, polytetrafluoroethylene (Teflon TM), poly(methylmethacrylate) (Plexiglass TM), poly(ethyleneterephthlate) (Mylar TM), glass, poly(butylterephthalate) (Valox TM), and the like. Preferably, because of the possibility of fire, the material for the lock notch-spacer of the present invention should be a nonflammable material such as polycarbonate, polytetrafluoroethylene (Teflon TM), poly(ethyleneterephthlate) (Mylar TM), glass, poly(methylmethacrylate) (Plexiglass TM), poly(butylterephthalate) (Valox TM), and the like. Most preferably, the lock notch-spacer of the present invention is made from poly(butylterephthalate) (Valox TM).

Figures 4A, 4B:
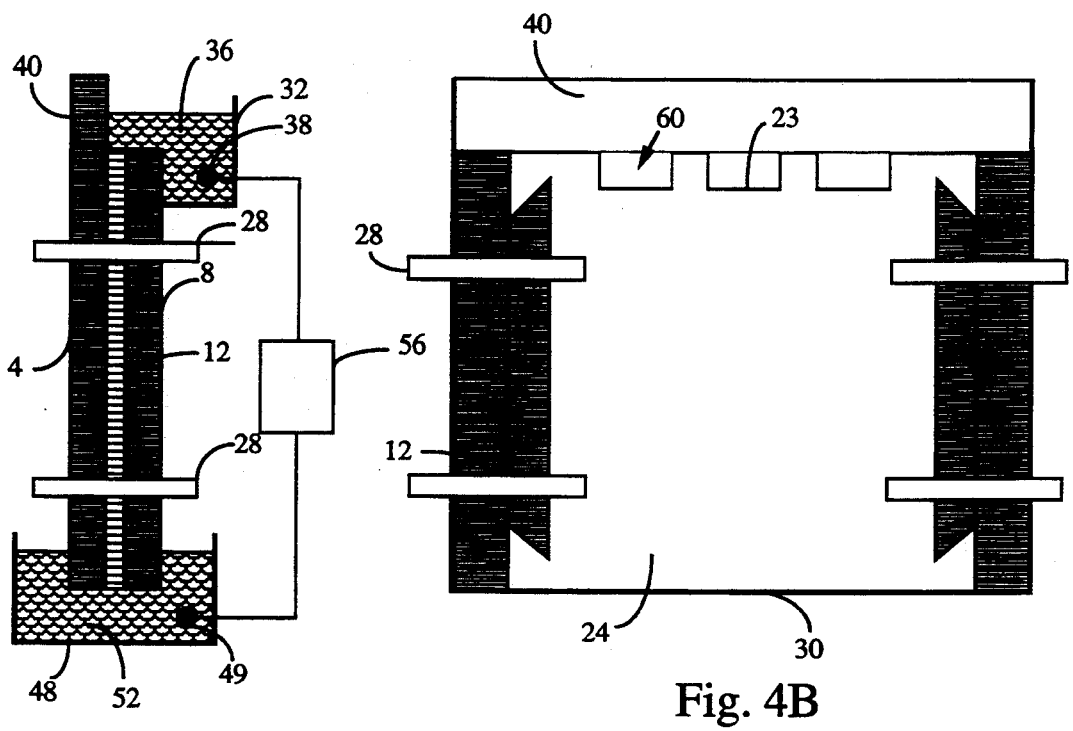
FIG. 4 (A and B) both front and side views of a slab gel electrophoresis apparatus incorporating the side spacer of the present invention.

FIG. 4 shows a slab gel sandwich used for electrophoretic separations which uses the present invention. Front and back plates (4) and (8), are brought together facing one another and separated by lock-notch spacers (12). Plates (4) and (8) should be flat, and be made from a non-porous, electrical insulator which does not adversely interact with the gel material or the sample molecules. Typically, plates (4) and (8) are formed of glass.

Lock-notch-spacers (12) are placed between front and back plates (4) and (8) to provide a uniform gap between the plates into which the gel is formed. Typically, lock-notch spacers (12) have a thickness of between 100 μm and 5000 μm. In a preferred embodiment, two lock-notch spacers (12) are provided, one on each side of gel layer (24).

To form gel layer (24), the edges of front and back plates (4) and (8) are clamped together so that the gel material cannot escape through the sides. Side clamps (28) are used to hold plates (4) and (8) in contact with lock-notch spacers (12), forming a leak-proof seal. In some cases, the side clamps can be replaced by adhesive tape. Preferably, tape is applied to bottom edge (30) of the gel sandwich during the pouring process to ensure that the medium does not leak out the bottom of the sandwich. A suitable separation medium, such as polyacrylamide or agarose, and the like, is used to fill the space between from and back plates (4) and (8). These materials are a flowable liquid when they are placed between the plates, after which the materials solidify to form a rigid gel. Typically, the separation medium is placed between the plates while the plates are in a vertical orientation, thereby facilitating the removal of gas bubbles present in the material.

Top reservoir (32) containing top buffer solution (36) and top electrode (38) is located at the top of the gel sandwich to provide an electrical connection between top edge (23) of gel layer (24) and top electrode (38). Typically, the reservoir is formed between upper extension (40) of front plate (4) and top reservoir (32).

Once the gel layer has solidified, the tape covering bottom edge (30) is removed and bottom edge (30) is immersed in bottom reservoir (48). Bottom reservoir (48), which contains bottom buffer solution (52) and bottom electrode (49), is located at the bottom of the gel sandwich to provide an electrical connection between bottom edge (30) of gel layer (24) and bottom electrode (49).

A voltage source (56) connects top electrode (38) and bottom electrode (49). Voltage source (56) should be capable of providing DC voltages of between about 100 and 5000 V and total power output up to about 500 W.

Normally, several samples are run through the gel simultaneously in multiple parallel lanes. Each lane is defined by a sample well (60) formed at the top of gel layer (24) into which samples are loaded prior to electrophoresis. Sample wells (60) may be formed by a comb; a piece of thin plastic, equal in thickness to locknotch spacers (12), which is cut so as to form the well configuration in FIG. 4. Alternative well geometries can be used such as the "sharks tooth" configuration generally used in the field of nucleic acid sequencing. The comb is inserted between plates (4) and (8) after the liquid separation medium has been poured but before the gel hardens. After the gel has hardened, the comb is removed to leave the wells into which the sample can be placed prior to electrophoresis.

There has been described a new side spacer for use with slab gel electrophoresis apparatus which has advantages over side spacers previously used. Although the invention has been illustrated by the foregoing description, it is not to be construed as being limited to the materials employed therein, but rather the invention is directed to the generic area as hereinbefore disclosed. Various modifications and embodiments thereof can be made without departing from the spirit or scope thereof.

We claim:

1. A side spacer for an electrophoresis apparatus comprising: an inside edge which contacts a gel layer, the inside edge having at least one notch which inscribes a hold area anchoring the side spacers into the gel layer.

2. The side spacer of claim 1 wherein said hold area of said notch is between $1*10^{-6}$ m$^2$ and $1.2*10^{-3}$ m$^2$.

3. The side spacer of claim 1 wherein at least one notch is located within 20 cm of a top edge of a gel layer.

4. The side spacer of claim 1 wherein at least one notch is located within 20 cm of a bottom edge of a gel layer.

5. The side spacer of claim 1 wherein said notch is a triangular notch having a notch edge, wherein the notch edge has a length of between 5 mm and 50 mm, and a notch angle, wherein the notch angle is an acute angle.

6. The side spacer of claim 5 wherein said notch angle is between 5° and 45°.

7. The side spacer of claim 5 wherein the notch angle is 45°.

8. The side spacer of claim 1 comprising an electrically non-conducting, non-compressible, and chemically inert material.

9. The side spacer of claim 8 wherein said material is selected from the group consisting of polycarbonate, polyvinylchloride, polytetrafluoroethylene (Teflon TM), poly(methylmethacrylate) (Plexiglass TM), poly(ethyleneterephthlate (Mylar TM), glass, and poly(butylterephthalate) (Valox TM).

10. The side spacer of claim 8 wherein said material is selected from the group consisting of polycarbonate, polytetrafluoroethylene (Teflon TM), poly(methylmethacrylate) (Plexiglass TM), poly(ethyleneterephthlate (Mylar TM), glass, and poly(butylterephthalate) (Valox TM).

11. The side spacer of claim 8 wherein said material is poly(butylterephthalate) (Valox TM).

12. An electrophoresis gel sandwich, comprising:
   (a) a pair of juxtaposed flat plates with a gel layer therebetween;
   (b) a pair of side spacers having at least one notch for spacing the plates apart and parallel to each other, the notch inscribing a hold area anchoring the side spacer into the gel layer.

* * * * *